(12) United States Patent
Avram

(10) Patent No.: US 6,686,392 B1
(45) Date of Patent: Feb. 3, 2004

(54) LIPIDIC ZINC COMPOUNDS AND USE FOR TREATMENT OF PROSTATIC HYPERTROPHY

(76) Inventor: Elena Avram, 545 W. End Ave., Apt 8E, New York, NY (US) 10024

( * ) Notice: Subject to any disclaimer, the term of this patent is extended or adjusted under 35 U.S.C. 154(b) by 0 days.

(21) Appl. No.: 10/261,958

(22) Filed: Oct. 1, 2002

(51) Int. Cl.⁷ ............................................. A61K 31/315
(52) U.S. Cl. ........................................ 514/494; 554/75
(58) Field of Search ............................ 514/494; 554/75

(56) References Cited

U.S. PATENT DOCUMENTS

| | | | |
|---|---|---|---|
| 4,255,419 A | 3/1981 | Leopold | 424/145 |
| 4,677,118 A | 6/1987 | Revici | 514/499 |
| 5,411,748 A | 5/1995 | Song | 424/559 |
| 5,997,908 A | 12/1999 | Song | 424/559 |

OTHER PUBLICATIONS

Costello, L.C. et al., "Novel Role of Zinc in the Regulation of Prostate Citrate Metabolism and its Implications in Prostate Cancer," Prostate 1998 Jun. 1;35(4):285–96.

Habib, F.K. et al., "Cancer of the Prostate: Early Diagnosis by Zinc and Hormone Analysis?, " Br J Cancer 1979 Jun.;39(6):700–4.

Leake, A. et al., "Interaction Between Prolactin and Zinc in the Human Prostate Gland," J Endocrinol 1984 Jul.;102(6):73–6.

Leissner, K.H., "Connection and Content of Zinc in the Human Prostate," Invest Urol 1980 Jul.;18(1):32–5.

Marczynska, A. et al., "The Concentration of Zinc in Relation to Fundamental Elements in the Diseased Human Prostate," Int. Urol Nephrol 1983;15(3):257–65.

Ogunlewe, J.O. et al., "Zinc and Cadmium Concentrations in Indigenous Blacks with Normal, Hypertrophic, and Malignant Prostate," Cancer 1989 Apr. 1;63(7):1388–92.

Revici, Emanuel, Research in Physiopathology as Basis of Guided Chemotherapy *With Special Application to Cancer*, p. 401–402 (D. Van Nostrand Company, Inc.) (1961).

Zaichick, VYe et al., "Zinc in the Human Prostate Gland: Normal, Hyperplastic and Cancerous," Int. Urol Nephrol 1997;29(5):565–74.

*Primary Examiner*—Deborah D. Carr
(74) *Attorney, Agent, or Firm*—Winston & Strawn LLP

(57) ABSTRACT

A method for making a composition containing a fatty acid or fatty ester compound and zinc. The compositions produced by the method. Administration of these compositions to a patient to increase the zinc content of cells or tissue having a zinc deficiency or to treat at least some of the symptoms of diseases or adverse effects caused by this zinc deficiency.

18 Claims, No Drawings

LIPIDIC ZINC COMPOUNDS AND USE FOR TREATMENT OF PROSTATIC HYPERTROPHY

FIELD OF THE INVENTION

The present invention relates to a method to treat various conditions resulting from zinc deficiency and preparation of the same. In particular, the invention relates to the administration of novel zinc-in-oil or lipidic zinc reaction products for the treatment of benign prostatic hypertrophy.

BACKGROUND OF THE INVENTION

While zinc has heretofore been referred to as a trace element in human nutrition, in reality its concentration in humans is second only to that of iron in the metals. Zinc concentration in a prostate gland is much higher than in other human tissues.

Benign prostatic hypertrophy (BPH) is a common disorder of elderly men, affecting about 80% of men by the age of 80. It is a common histologic condition which conveys its morbidity through lower urinary tract symptoms and complications, such as acute urinary retention, obstructive uropathy, and urinary tract infections. Until recently, therapeutic options were limited, and transurethral surgery was the most common remedy.

Although zinc concentration in a prostate is usually high, it is reduced in pathological conditions, such as BPH. Available water-soluble zinc compounds when administered to a subject have minimal action upon lesions in therapeutic need of zinc because they are not taken up effectively by free lipids in the abnormal cells. Because of limited clinical results in reduction of prostate volume, zinc has remained unproven as an effective therapy in this condition. Thus, improved formulation and treatment methods are needed.

SUMMARY OF THE INVENTION

The present invention now addresses this problem by providing new formulations and treatment methods for administering zinc to a subject. It has now been discovered in the present invention that zinc can be administered by way of a simple formulation where zinc is incorporated into a lipid by bonding zinc to the non-polar part of the lipid. It has also been found that lipid-incorporated zinc is much more active biologically than non-lipidic formulations that contain zinc.

The present invention thus relates to novel compositions of lipids which include zinc incorporated therein. There compositions zinc-in-oil or lipidic zinc reaction products that are made by adding a zinc compound to a lipid component and heating the lipid component to a temperature of at least about 260° C. for a sufficient time to incorporate a predetermined amount of zinc into the lipid. As least about 0.1% zinc by weight can be incorporated, although between 1 and 10% zinc by weight are preferred.

The compositions of the invention may be administered to a patient who has cells or tissues that are deficient in zinc. One particular treatment, for example, is the administration of the compositions of the invention to a subject experiencing symptoms of BPH. The incorporated lipidic zinc is taken up preferentially by free lipids in abnormal cells or tissues, thus providing an effective treatment of BPH or other pathological conditions involving zinc deficiency.

DETAILED DESCRIPTION OF THE PREFERRED EMBODIMENTS

In general, abnormal cells and tissues in the body have free lipids. Thus, the invention is based on the recognition that a lipid or compound having a lipidic character introduced into the body can be selectively taken up by these abnormal cells.

Zinc intervenes in the body's action against pathological conditions. In these cases, zinc is mobilized from different parts of the body in the form of lipidic compounds, and these lipidic-zinc compounds are taken up specifically by lesions through abnormal free lipids contained in the lesions. Insufficient intervention of zinc in the body's defense against such lesions is due to the insufficient lipidic action of currently available zinc formulations. Accordingly, zinc compound having lipidic properties have been found to be useful as a therapeutic agent for patients who have zinc deficient pathological conditions such as BPH.

Zinc can be incorporated in the molecule of a fatty acid by heating together an organic or inorganic salt of zinc with a lipid. Preferably, the lipid is previously oxidized by being heated and mixed with air or oxygen. The mixtures of zinc and lipids are heated at a temperature of at least about 260° C. for a time until an exothermic reaction is observed, which reaction indicates the incorporation is taking place.

Examples of the zinc/lipid compositions that can be used according to the invention include the reaction products of allylic unsaturated lipids and a zinc compound. These reaction products are produced by heating a liquid composition containing a lipid, structurally characterized by allylic unsaturation with a zinc salt. Any zinc salt may be used in the invention, preferably, the zinc salt is an organic zinc salt such as zinc acetate or zinc carbonate. The liquid is preferably oxidized for example, by bubbling air or oxygen through the reaction mixture.

The allylic unsaturated compound is preferably a naturally occurring oil containing polyunsaturated fatty esters, such as an animal, vegetable, or fish oil, and particularly, polyunsaturated vegetable oils. Safflower oil, a vegetable oil, is the most advantageous oil for use in the present compositions in the practice of this invention.

The composition utilized should contain a significant percentage of molecular species having allylic moieties to render the compositions useful according to the invention. Such moieties are indicated by the following partial structures —CH=CH—CH$_2$—CH=CH— and/or —CH=CH—CH=CH—CH$_2$—. As indicated, the unsaturation can be conjugated or nonconjugated, but the composition must contain allylic methylene hydrogens.

Such compositions may initially be oxidized or heated in the presence of air or oxygen at the temperature range between about 100° C. and about 150° C. The oxygen can be obtained by merely heating the composition in a vessel which is open to the atmosphere, but preferably and advantageously, the source of oxygen is a gas such as air which is introduced into the oil with agitation, during the heating step. Oxygen or air can be injected into the heated oil as the introduction of air provides a source of agitation. Additional mixing or agitation can also be provided.

The heating step is conducted for a period of from about 15 minutes to about two hours. The temperature should be maintained at an upper limit within the range of about 260° C. to 280° C., and preferably about 265° C. to 270° C. These temperature limitations are based on a heating time of about one-half hour. The temperatures can be altered within limits depending on the time of heating. For example, when the temperature is about 265° C., the time is about one-half hour, while temperatures as high as 270° C. require a shorter period of time for heating. Higher temperatures for a prolonged period of time tend to degrade the composition and should thus be avoided.

Agitation, by stirring for example, aids in the reaction, and experiments to date indicate that a fairly violent stirring is advantageous. The introduction of air into the mixture during the heating is also very advantageous, particularly when the mixture is not subject to prolonged heating and thus, is the preferred method. The mixing or stirring can be accomplished with the introduction of the air.

After the reaction has taken place, the mixture is cooled. The remaining fluid is ready for use after appropriate sterilization for injection or incorporated into capsules, such as gelatin, for oral administration.

The precise nature of the compositions which result from the above-described treatment or the identity of the effective component or components is not presently known. It is known, however, that these compositions do include zinc. Although any amount above 0.1% of zinc incorporated into the composition is useful, a proportion of zinc in the range of about 1 to 10 weight percent has been found to be preferred. As mentioned above, although any zinc salt may be used, but an organic salt of zinc, such as zinc carbonate or zinc acetate, is preferred, with the zinc bonding the eleostearic acid present in the oil.

The products obtained have the zinc incorporated in general at the level of the double bonds of the different unsaturated fatty acids, this causes their toxicity to be exceptionally low. The injection of 0.3 ml of a production having 2% zinc to a mouse does not kill it.

The incorporated zinc composition may be administered orally, by injection, sublingually or rectally in the appropriate formulation.

The incorporated zinc is believed to be absorbed by the abnormal cells, thus compensating for their low zinc content. This treatment produces objective and subjective improvement in the conditions, of patients having a variety of disease based upon such abnormal cells. BPH is an example of diseases in which low cellular zinc abnormal cells are found. By increasing cellular calcium, the progression of BPH is slowed.

Such low cellular zinc abnormal cells are believed to cause an anabolic imbalance in the body. This anabolic imbalance can be analyzed and diagnosed by blood and urine analyses. A low eosinophilia (above 100/cmm), a low red cell sedimentation rate (below 15 ml/1 hour), a low serum potassium (below 4.5 mEq), a urine alkaline pH (above 7), low specific gravity (below 1.016), high surface tension (above 89 dynes/cm), and high calcium or chloride excretion are indications of an anabolic imbalance. (The opposite analyses would indicate a catabolic imbalance.)

These analyses and clinical manifestations have to be changed by the administration of the incorporated zinc compound. In a 2% zinc incorporated preparation, amounts from about 2 to 10 ml daily are predilectly used for the treatment of this anabolic imbalance. For other conditions with catabolic imbalances, doses from about $\frac{1}{10}$ to 2 ml daily are predilectly used. In general the higher the dose used, the better are the clinical results.

In addition to successful treatment of BPH, good results were also obtained in the use of the incorporated zinc compounds to treat other pathological conditions where all available zinc products have proven of very limited help. For example, lipid-incorporated zinc may be used for topical administration, as a cream or a lotion, in the treatment of dermatoses and for the prevention and treatment of skin-aging manifestations.

The incorporated zinc composition may be administered together with different additional agents, including analgesics, vitamins, minerals, antioxidants and the like.

Specific preferred additional agents include epichlorohydrin (i.e., 1-chloro 2,3-epoxy propane), magnesium thiosulfate, or n-butanol. It is preferable that hydrolyzed epichlorohydrin is incorporated in the zinc composition and that at least about 0.05% by weight of hydrolyzed epichlorohydrin, and more preferably that between about 0.1 and 1.5% by weight is incorporated in the zinc composition. These amounts have been found to be advantageous, but can be higher or lower if desired.

EXAMPLES

The following examples demonstrate the effectiveness of the zinc-in-oil or lipidic zinc reaction products for the treatment of patients having been diagnosed as having BPH and prostate cancer and having at least a P.S.A. of 4. The patients were given 1 capsule, four times a day of lipidic zinc with epichlorohydrin. The capsule size is 00 and it contains 20 to 22 drops of a 2% by weight incorporated zinc product.

Example 1

A 43 year old man was diagnosed on with BPH and prostate cancer. He was experiencing pain and frequency in urination, and had a P.S.A. of 4.2. The patient was treated with 1 capsule 00- 4 times per day. The symptoms responded within a few weeks, as evidenced by a P.S.A. that was reduced to 3.00. While on treatment, the patient was doing very well.

Example 2

A 70 year old man was diagnosed with BPH and prostate cancer. Treatment was begun with 1 capsule 00, 4 times daily. Improvements in symptoms were noted in that the patient experienced less urination frequency and was sleeping better. P.S.A. 1/02/01 was measured as 10.7, but no metastases was noted.

During a later phase of treatment, the P.S.A. was measured as 20. The dosage was doubled, with 2 capsules 00 given 4 times per day. Patient continued treatment and five months later, P.S.A. was measured as 2.4.

Example 3

A 67 year old man was diagnosed with BPH and prostate cancer. His P.S.A. measured 8.4 and he was experiencing frequent urination and pain. The initial treatment was for 1 capsule 00 administered 4 times per day. After a few weeks, patient was doing well, with pain reduced. P.S.A. measurements fluctuated between lower and higher values, but no metastasis was found and the cancer was in total remission after six months treatment. The treatment was then modified to one capsule 00 taken each night.

Example 4

A 63 year old man diagnosed with BPH and cancer of the prostate. He had a P.S.A. of 4, and was experiencing frequency in urination and disuria. He was given 1 capsule 00 of four times a day. The symptoms responded within a few days. After 7 months treatment, the patient was doing well with greatly reduced pain and lesser frequency of urination.

Example 5

A 60 year old man diagnosed with BPH and cancer of the prostate. P.S.A. was measured as 7.34, and like the others he complained of pain, disuria and frequency of urination. He was given 1 capsule 00 four times a day for 2 months. The patient responded and the symptoms were controlled.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method of preparing a zinc and oil reaction product for pharmaceutical use which comprises heating an animal, vegetable or fish oil having an allylic unsaturation of the type $-CH=CH-CH_2-CH=CH-$ and/or $-CH=CH-CH=CH-CH_2-$ and a zinc compound at a temperature of between about 260° C. and 280° C. for between about 15 minutes and 2 hours to incorporate by exothermic reaction between about 0.1 and 10% by weight zinc into the oil.

2. The method of claim 1 wherein the zinc salt is an organic salt and the oil is oxidized before the zinc compound is added by mixing the oil with air and heating the mixture.

3. The method of claim 1 wherein the mixture is oxidized by introducing air into the mixture while heating at stated temperature and time ranges.

4. The method of claim 1 wherein the oil is a vegetable oil and the heating step is conducted to incorporate at least 1% by weight of zinc into the oil.

5. The method of claim 1 further comprising the step of adding epichlorohydrin to the mixture.

6. The method of claim 5 wherein at least about 0.05% by weight of epichlorohydrin is incorporated into the mixture.

7. The method of claim 1 which further comprises agitating the mixture during the heating step.

8. The method of claim 1 wherein the zinc compound is zinc acetate.

9. A lipidic zinc composition comprising at least an animal, vegetable or fish oil having an allylic unsaturation of the type $-CH=CH-CH_2-CH=CH-$ and/or $-CH=CH-CH=CH-CH_2-$ which includes zinc incorporated therein in an amount of at least 0.1% by weight.

10. The lipidic zinc composition of claim 9 further comprising epichlorohydrin.

11. The composition of claim 10, wherein at least about 0.05% by weight is epichlorohydrin.

12. The zinc and oil reaction product produced by the method of claim 1.

13. The zinc and oil product of claim 12 further comprising epichlorohydrin.

14. The product of claim 13, wherein at least about 0.05% by weight is epichlorohydrin.

15. A method for increasing the zinc content of cells or tissue having a zinc deficiency which comprises administering to a patient having said zinc deficient cells or tissue a therapeutically effective amount of the composition of claim 9.

16. The method of claim 15 wherein about 1/10 to 10 ml of the composition is daily administered to the patient.

17. A method for increasing the zinc content of cells or tissue having a zinc deficiency which comprises administering to a patient having said zinc deficient cells or tissue a therapeutically effective amount of the composition of claim 12.

18. The method of claim 17 wherein about 1/10 to 10 ml of the composition is daily administered to the patient.

* * * * *